US00PP36376P3

(12) United States Plant Patent
Hansen

(10) Patent No.: US PP36,376 P3
(45) Date of Patent: Jan. 7, 2025

(54) **X *HANSARA* PLANT NAMED 'JUMPING JACK FLASH'**

(50) Latin Name: **x *Hansara* hybrid**
Varietal Denomination: Jumping Jack Flash

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 360 days.

(21) Appl. No.: 18/455,126

(22) Filed: Apr. 17, 2023

(65) Prior Publication Data

US 2024/0349633 P1 Oct. 17, 2024

(51) Int. Cl.
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/02
See application file for complete search history.

*Primary Examiner* — Keith O. Robinson

(57) ABSTRACT

A new and unique x *Hansara* plant named 'Jumping Jack Flash' characterized by compact mounded habit and upright curving, lanceolate foliage with grayish-green color and in high ultraviolet light exposure developing margins of burgundy speckling on top and bottom. The leaf tips are narrowly acute without mucros. The marginal teeth are small and flexible. The plant is suitable as a potted plant patio, for the garden, or for use as a houseplant.

3 Drawing Sheets

Botanical classification: x *Hansara* hybrid.
Variety denomination: 'Jumping Jack Flash'.

STATEMENT REGARDING PRIOR DISCLOSURES UNDER 37 CFR 1.77(b)(6)

No plants of x *Hansara* 'Jumping Jack Flash' have been sold, in this country or anywhere in the world. No disclosure of the new plant or offer for sale has been made, more than one year prior to the filing date of this application, and such disclosure within one year was either derived directly or indirectly from the inventor and would therefore be a 35 USC § 102(b) exception.

BACKGROUND OF THE INVENTION

The present invention relates to the new and distinct x *Hansara* 'Jumping Jack Flash' discovered by the inventor on Feb. 21, 2021, at a wholesale perennial nursery in Zeeland, Michigan, USA. The new plant is a variegated whole plant mutation of the tri-generic hybrid x *Hansara* 'Jumping Jacks' U.S. Plant Pat. No. 31,628 initially identified by the breeder code 21-SP-HANS-1024. The new plant has been successfully asexually propagated initially in 2022 by separation of offshoots and also by sterile shoot tissue culture at the same nursery in Zeeland, Michigan. Both methods of asexual propagation systems have been found to produce stable and identical plants that maintain all the unique characteristics of the original plant in successive generations.

BRIEF SUMMARY OF THE INVENTION

X *Hansara* 'Jumping Jack Flash' differs from its parents as well as all other *Manfreda, Agave, Polianthes,* and x

*Mangave* known to the applicant. The most similar known cultivars known to the inventor are: the parent 'Jumping Jack', the x *Mangave* hybrids 'Bad Hair Day' U.S. No. 30,279, 'Freckles and Speckles' U.S. Plant Pat. No. 30,904, 'Pineapple Express' U.S. Plant Pat. No. 28,613, 'Dragon Lady' U.S. Plant Pat. No. 33,985, 'Queen for a Day' U.S. Plant Pat. No. 32,711, and *Polianthes* x *bundrantii* 'Opal Eyes' (not patented).

'Bad Hair Day' has narrower foliage with much more arching habit and burgundy spotting throughout. 'Freckles and Speckles' has stiffer, shorter, less upright, slightly broader foliage with spotting throughout. 'Pineapple Express' has shorter, thicker, broader leaves with larger spots throughout. 'Dragon Lady' has more arching and more sinuate foliage with leaf margins that develop large, dense, dark greyed-purple spotting on a glaucous, light greyed-purple background, the leaf centers are variegated with creamy-yellow and cherry-red spots. 'Queen for a Day' has larger, broader, and more arching leaves with large marginal teeth and the margin develops to a nearly solid burgundy. *Polianthes* 'Opal Eyes' has foliage that is narrower and more flexible without marginal teeth or spotting on the margin.

The parent has similar foliage with the burgundy spotting throughout.

The new plant 'Jumping Jack Flash' is unique from all of these above cultivars and all *Agave*, x *Mangave*, and *Manfreda* is known to the inventor by the following combined traits:

1. Compact habit with upright curved leaves;
2. Foliage lanceolate with small flexible marginal teeth;
3. Foliage develops burgundy speckled variegation on the top and bottom margins of glaucous green leaves;
4. Leaves are succulent and slightly fleshy;
5. Yellowish flowers from orangish-yellow buds on stiff, tall, branched scapes;
6. Rapid growth rate.

BRIEF DESCRIPTION OF THE DRAWINGS

The photograph of the new plant demonstrates the overall appearance of the new plant including the unique traits as a two-year-old plant grown in a container in a greenhouse with supplemental water and fertilizer and moved to a full-sun trial garden for summer growth. The colors are as accurate as reasonably possible with color reproductions. Ambient light spectrum, temperature, source, and direction may cause the appearance of minor variations in color.

DETAILED BOTANICAL DESCRIPTION

Figure 1:
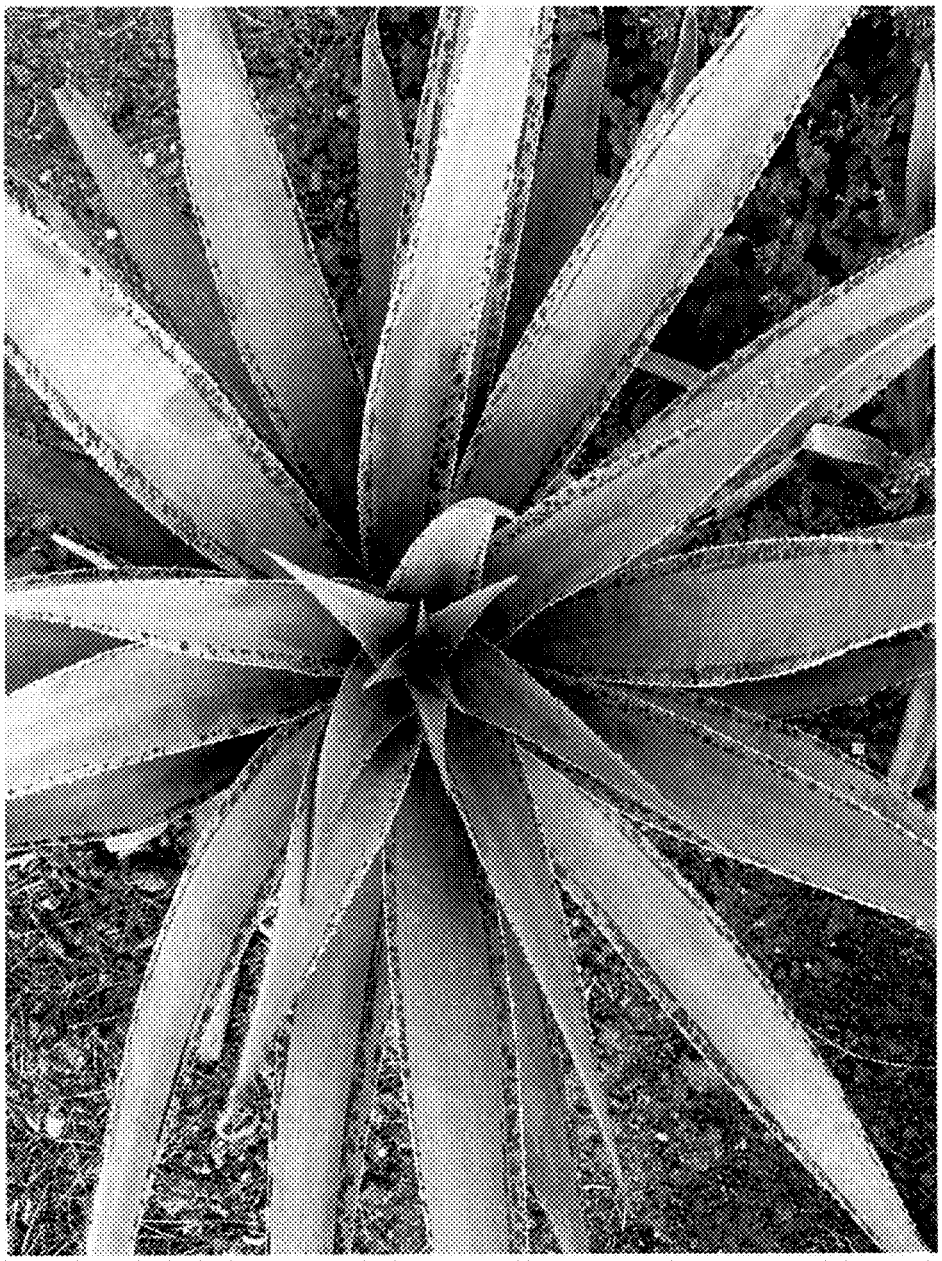
FIG. 1 shows the new plant in a container from above with a close-up of the foliage.
Figure 2:
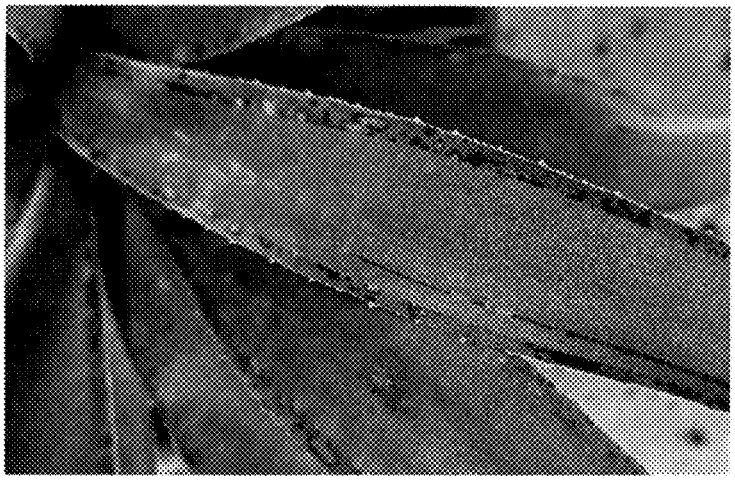
FIG. 2 shows a close-up of the leaf margin with spots and teeth.
Figure 3:
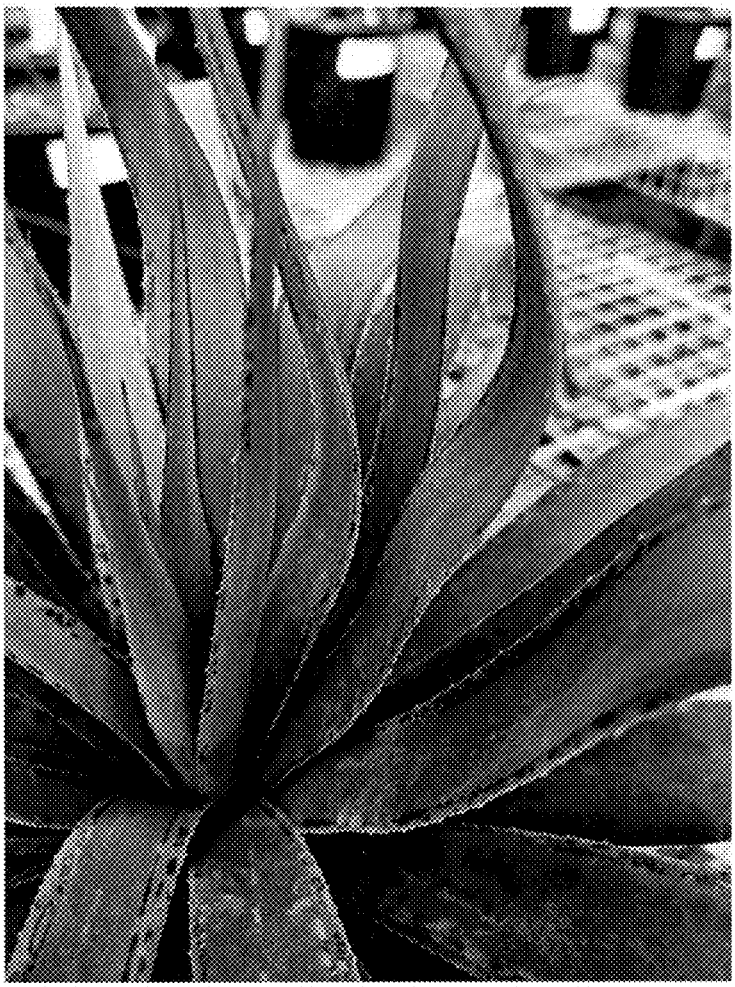
FIG. 3 shows the new plant from a side view with young upright curving foliage.
Figure 4:
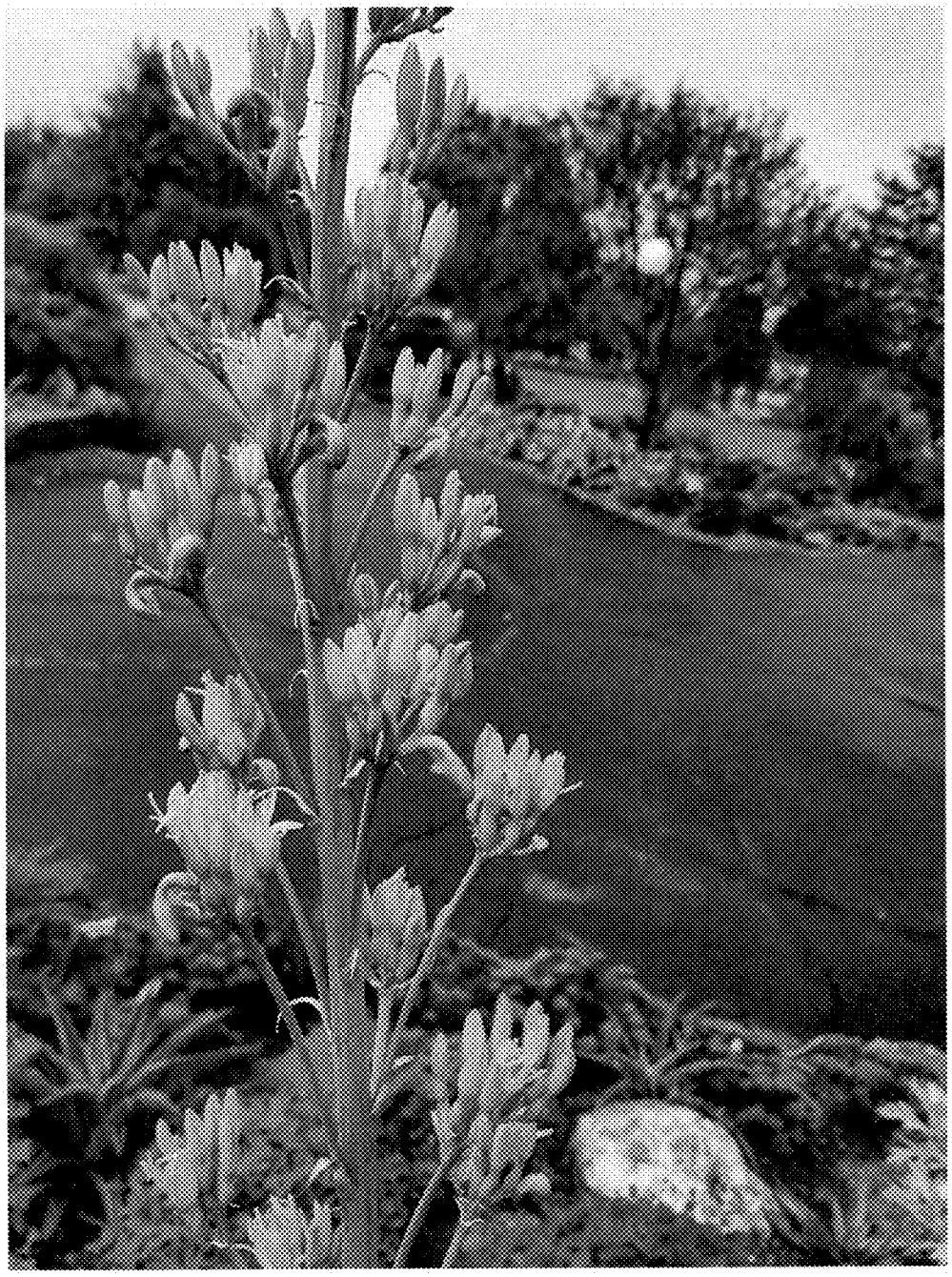
FIG. 4 shows the flowers and buds on the scape of the new plant.

The following descriptions are of a three-year-old plant in a commercial wholesale greenhouse and in a full-sun trial garden in Zeeland, Michigan using color references based on the 2015 edition of The Royal Horticultural Society Colour Chart except where common dictionary terms are used. The new plant, x *Hansara* 'Jumping Jack Flash', has not been observed under all possible environments. The phenotype may vary slightly with different environmental conditions, such as temperature, light, fertility, moisture, and maturity levels, but without any change in the genotype.

Parentage: Whole plant mutation of x *Hansara* 'Jumping Jacks';

Propagation: Division and sterile shoot tissue culture;

Time to initiate roots from tissue culture: About 21 days;

Growth rate: Rapid;

Crop time: About 12 to 14 weeks to finish during lengthening spring days from an established 25 mm tissue culture plug to a 65 mm diameter container;

Rooting habit: Fleshy and fibrous, with roots up to 15 cm long;

Root color: Nearest RHS 158C depending on soil type;

Plant shape and habit: Succulent herbaceous perennial with basal rosettes of about 57 fleshy leaves radially emerging and curving upwardly from central shortened stem, producing a symmetrical rounded mound;

Plant size: Foliage height about 31 cm tall from soil line to the top of the leaves and about 42 cm wide at the widest point above soil line;

Stem: To about 3.5 cm across; covered in leaves;

Foliage description: Lanceolate; simple; slightly fleshy; glaucous; glabrous; margins finely dentate with flexible teeth; narrowly apex acute with flexible tip; base truncate, sessile, clasping;

Leaf size: To about 27 cm long, about 35 mm wide at base and 3.5 mm thick, average about 25 cm long, 27 mm wide and 3 mm thick; usually bi-laterally symmetrical; glabrous and glaucous above and below; spots of variable sizes from about 0.5 mm diameter to about 4 mm long and 3 mm across, frequently overlapping; spotted margin to 5 mm wide on adaxial and 2 mm wide on abaxial with center adaxial to 25 mm wide and center abaxial to 31 mm wide;

Marginal teeth: Flexible; variable sizes between about 1 mm long and 1 mm wide at base, about 6 mm apart; with an average of about three smaller teeth about 0.5 mm long and 0.5 mm across at base between larger teeth;

Foliage fragrance: None observed;

Leaf blade color:

*Adaxial* (*young*).—Between RHS 189B and RHS 189C with marginal spots of nearest RHS N187B and thin marginal color between RHS 187B and RHS 187C.

*Abaxial* (*young*).—Between RHS 189B and RHS 189C with marginal spots between RHS N187C and RHS N187B.

*Adaxial* (*mature*).—Nearest RHS N138C, with marginal spots of between RHS187B and RHS N187C.

*Abaxial* (*mature*).—Nearest RHS N138C, with marginal spots of nearest RHS 189A in lower ultraviolet light and nearest RHS 187B to blend between RHS N187 to RHS N187B with high ultraviolet light.

*Teeth*.—Larger and smaller teeth variable, both abaxial and adaxial nearest RHS N186C and blend between RHS 186D and RHS NN155B.

Apical spine: Absent;

Petiole: Sessile;

Veins: Parallel; not distinct;

Peduncle: Terete; glaucous; glabrous; stiff; strong; lightly branched; about 158 cm long and 17 mm diameter at base and 13 mm diameter below first flowers; flowering portion about 80 cm tall and about 13.0 cm across; about 36 branches to about 14 cm long and about 5 mm diameter at base; attitude main peduncle and branches upwards, erect;

Peduncle color: Flowering portion and below flowering portion nearest RHS 147C;

Pedicel: Terete; glaucous; glabrous; stiff; strong; upright; average about 5 mm long and 2.5 mm diameter;

Pedicel color: Nearest RHS 147C;

Cauline leaves: About 40 per scape below flowers; lanceolate; simple; slightly fleshy; glaucous; glabrous; distally slightly recurved downward away from stalk; margins finely dentate with flexible small and tiny teeth; apex narrowly acute; base truncate, sessile, clasping; proximally about 18 cm long and about 15 mm wide at base, decreasing distally; color adaxial and abaxial and teeth same as basal leaves;

Buds one day prior to opening: Elongated globose; about 3 cm long and about 6 mm across at mid-tepal, base about 4 mm diameter;

Bud color: Distal portion between RHS 168D and RHS 168C, basal portion nearest RHS 138C;

Flower description: Perfect, incomplete; actinomorphic; about 4 cm long and opening to about 3 cm across; lasting about 3 to 4 days per flower; flowering period about three weeks in late winter in Michigan greenhouse or summer outdoor garden; producing abundant nectar; approximately 250 to 300 flowers per scape; attitude mostly upright;

Flower fragrance: Not detectable;

Tepals: Six, in two identical sets of three; glaucous abaxial and slightly lustrous adaxial; glabrous both adaxial and abaxial; acute apex and fused base; about 3 cm long, fused in basal 1.8 cm and about 5 mm wide just above fusion;

Tepal color: Adaxial outer and inner tepal set base between RHS 6D and RHS 6C with center and apical blushing between RHS 21C and RHS 21B; abaxial outer and inner set base surrounding ovary nearest RHS 138B with central and distal portion nearest RHS 22B;

Androecium: Six;

*Filaments*.—Six; terete distally, slightly applanate base; stiff and straight; about 3 cm long and 1 mm diameter at base; color nearest RHS 10B.

*Anther*.—Dorsifixed; longitudinal; about 8 mm long and 2 mm diameter before opening; after dehiscence curving backward; color nearest RHS 21D.

*Pollen*.—Abundant; color nearest RHS 21B.

Gynoecium: Single;

*Style*.—4.2 cm long and 1.5 mm diameter at base; color between RHS N163D and RHS 163B.

*Stigma*.—Turbinate, apex tri-lobed; about 2.5 mm tall and 3 mm across top; color nearest RHS NN155B.

*Ovary*.—Inferior.

Fruit: Tri-valved, loculicidal, dehiscent capsule; ellipsoidal; apex rounded; base rounded; about 9.0 mm long and 8.0 mm across;

Fruit color: When developing nearest RHS 137B; seed was harvested prior to dehiscence;

Seed: Slightly flattened, near round; about 2.0 mm across 1.2 mm thick; color lustrous, nearest RHS 202A;

Disease resistance: x *Hansara* 'Jumping Jack Flash' has not been observed to be resistant or susceptible to diseases common to other x *Hansara*, x *Mangave, Agave,* or *Manfreda.*

Growth: The plant is xeromorphic and survives well with minimal water once established.

Winter hardiness at least from USDA zone 9 to 11. The full extent of winter hardiness has not been tested.

I claim:

1. A new and distinct cultivar of ornamental x *Hansara* plant named 'Jumping Jack Flash' as herein described and illustrated.

* * * * *